US011642774B2

(12) United States Patent
Venticinque

(10) Patent No.: US 11,642,774 B2
(45) Date of Patent: May 9, 2023

(54) INTUBATION STYLETS

(71) Applicant: THE BOARD OF REGENTS OF THE UNIVERSITY OF TEXAS SYSTEM, Austin, TX (US)

(72) Inventor: Steven Venticinque, San Antonio, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 918 days.

(21) Appl. No.: 16/461,056

(22) PCT Filed: Nov. 16, 2017

(86) PCT No.: PCT/US2017/061967
§ 371 (c)(1),
(2) Date: May 15, 2019

(87) PCT Pub. No.: WO2018/094015
PCT Pub. Date: May 24, 2018

(65) Prior Publication Data
US 2020/0054849 A1 Feb. 20, 2020

Related U.S. Application Data

(60) Provisional application No. 62/423,061, filed on Nov. 16, 2016, provisional application No. 62/423,164, (Continued)

(51) Int. Cl.
A61B 1/00 (2006.01)
A61B 1/267 (2006.01)
(Continued)

(52) U.S. Cl.
CPC .......... *A61B 1/00066* (2013.01); *A61B 1/267* (2013.01); *A61M 16/0497* (2013.01);
(Continued)

(58) Field of Classification Search
CPC ..... A61B 1/00066; A61B 1/267; A61B 17/24; A61M 16/0488; A61M 16/0497; A61M 2205/586; B25G 1/102
See application file for complete search history.

(56) References Cited

U.S. PATENT DOCUMENTS 4,699,138 A * 10/1987 Behrstock ......... A61M 16/0418
604/902
5,470,328 A 11/1995 Furnish et al.
(Continued)

OTHER PUBLICATIONS

International Preliminary Report on Patentability Issued in Corresponding PCT Application No. PCT/US2017/061967, dated May 21, 2019.
(Continued)

*Primary Examiner* — Larry E Waggle, Jr.

(57) ABSTRACT

Certain embodiments are directed to a laryngoscopy device and methods of use thereof, the device having a curved, hollow stylet with a handle and a flexible bougie contained at least partially within the hollow stylet, the bougie being extendable out of the end of the stylet for use in guidance of a hollow endotracheal tube.

16 Claims, 12 Drawing Sheets

Related U.S. Application Data filed on Nov. 16, 2016, provisional application No. 62/560,182, filed on Sep. 18, 2017.

(51) Int. Cl.
*A61M 16/04* (2006.01)
*A61M 29/02* (2006.01)
*B25G 1/10* (2006.01)

(52) U.S. Cl.
CPC ............. *A61M 29/02* (2013.01); *B25G 1/102* (2013.01); *A61M 2205/586* (2013.01); *A61M 2250/00* (2013.01)

(56) References Cited

U.S. PATENT DOCUMENTS

| | | | |
|---|---|---|---|
| 5,551,946 A * | 9/1996 | Bullard | A61M 16/0418 600/187 |
| 5,735,873 A | 4/1998 | MacLean | |
| 6,616,634 B2 * | 9/2003 | Benz | A61M 5/3135 222/391 |
| 9,010,320 B2 * | 4/2015 | Furman | A61M 16/0418 128/200.26 |
| 2002/0068851 A1 | 6/2002 | Gravenstein et al. | |
| 2004/0215061 A1 * | 10/2004 | Kimmel | A61B 1/267 600/179 |
| 2009/0299400 A1 | 12/2009 | Wayman et al. | |
| 2011/0120458 A1 | 5/2011 | Schwartz et al. | |
| 2012/0078050 A1 * | 3/2012 | Schwartz | A61B 1/267 128/200.26 |
| 2013/0245372 A1 | 9/2013 | Lo | |

OTHER PUBLICATIONS

International Search Report and Written Opinion Issued in Corresponding PCT Application No. PCT/US2017/061967, dated Apr. 13, 2018.

Mort, "Emergency Tracheal Intubation: Complications Associated with Repeated Laryngoscopic Attempts," Anesthesia and Analgesia, 99; 607-613, 2004.

Partial European Search Report issued in corresponding European Patent Application No. 17872156, dated Jun. 24, 2020.

* cited by examiner

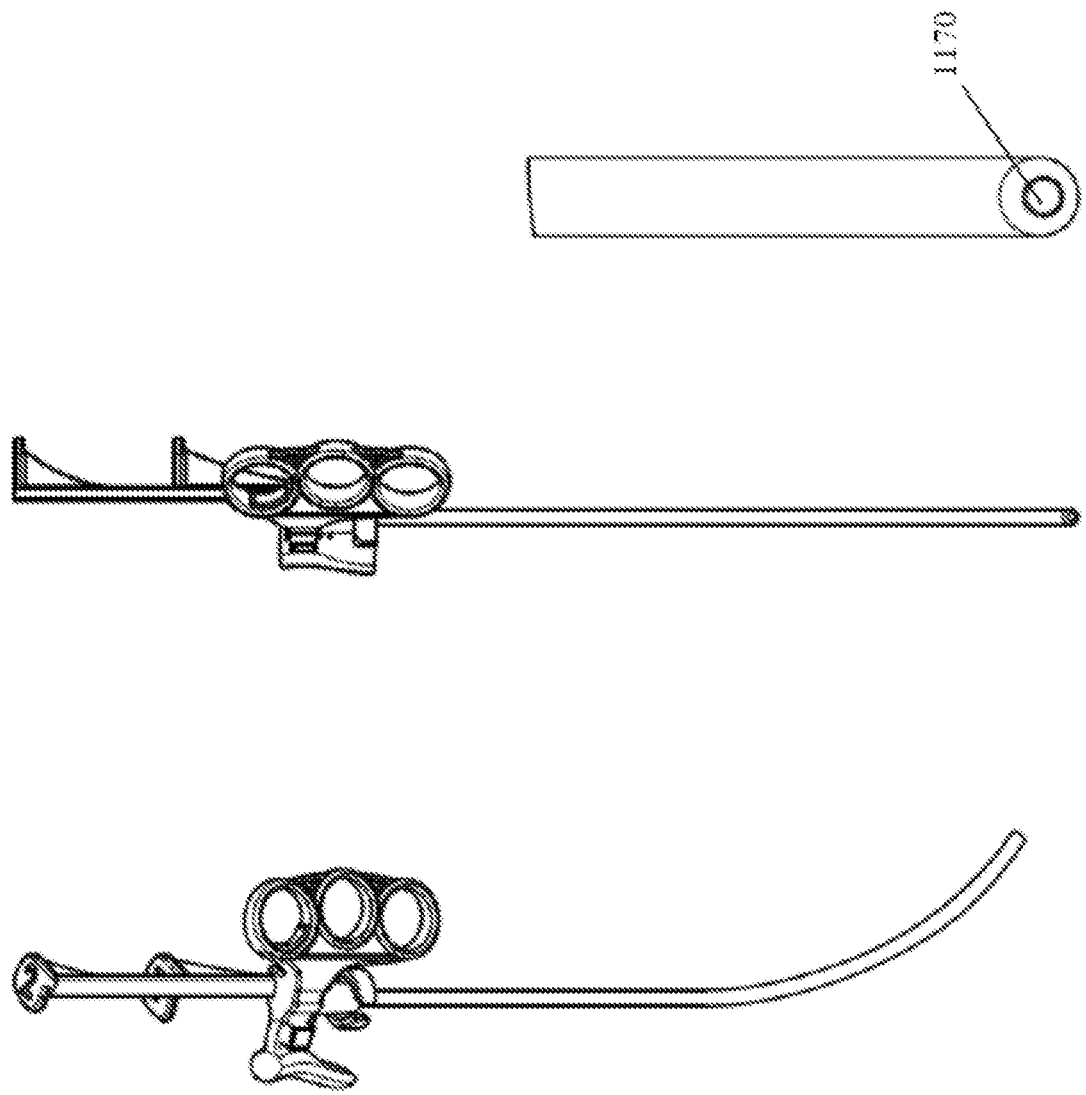

INTUBATION STYLETS

This application is a national phase application under 35 U.S.C. §371 of International Application No. PCT/US2017/061967, filed Nov. 16, 2017 which claims priority to U.S. Provisional Applications 62/423,061 filed Nov. 16, 2016; 62/423,164 filed Nov. 16, 2016; and 62/560,182 filed Sep. 18, 2017, each of which is incorporated herein by reference in its entirety.

BACKGROUND

Certain embodiments are directed to the field of medicine. In particular certain embodiments are directed to intubation assist devices.

Laryngoscopy can be used to assist tracheal intubation and involves the insertion of a laryngoscope to facilitate visualization of the vocal cords. This is followed by the insertion of an endotracheal tube (ETT) through the vocal cords into the trachea. Traditionally, direct laryngoscopy (DL) has been employed to expose the vocal cords so that operators can view them directly in order to insert an ETT. A metallic stylet is usually placed within the ETT to promote rigidity to assist insertion of ETT. The stylet is more rigid than the ETT and will maintain its shape under normal loading conditions. Occasionally, during DL operators are faced with patients having anatomic features that make visualization of the vocal cords difficult or impossible. These circumstances, along with advances in fiber-optic and digital camera technology, have led to the development of video laryngoscopy (VL), which employs laryngoscopes fitted with small cameras or fiber-optic bundles. VL's make viewing the glottic aperture easier despite challenging anatomic conditions or lower user skill. With VL even novice operators can more often visualize the vocal cords in circumstances where it would have been previously difficult to do so with DL. DL and VL are both used in day-to-day tracheal intubation practice.

VL continues to emerge as an increasingly accessible and utilized technique, particularly in circumstances of anticipated difficulty and during emergency airway management outside of the operating room. Although VL allows easier visualization of the vocal cords, a new challenge has emerged as a consequence of the technology. During DL the path to ETT insertion is a line-of-sight, 3-dimensional pathway, and only a minimal bend of the distal portion of the stylet and ETT is required. This results in compatibility between operator hand motion and desired outcome. However, with VL the cords are exposed with a camera or fiber-optic bundle located near the tip of the laryngoscope that is located out of the direct sight of the user. The resulting approach to the vocal cords can be up to 90 degrees offset from the insertion path, which requires more curvature of the ETT and stylet. Also, the procedure is now performed via a video screen instead of direct vision. The cumulative effect confines the operator to a discontinuous, 2-dimensional space, a spatially off-axis target, and dampened haptic feedback. This necessitates more complex movements and skill in order to engage the glottic aperture.

Another problem that sometimes arises with VL is that the resultant angle of the anterior larynx and the distal ETT can cause the ETT to collide with the anterior portion of the larynx impeding ETT advancement into the trachea. Difficulty advancing the ETT into the trachea when using VL is a well described phenomenon.

Operators can find themselves with an adequate view of the vocal cords and the ETT engaged within the glottic aperture, yet are unable to advance the ETT into the trachea. This can occur despite the use of rigid stylets designed specifically to accommodate the angle required to facilitate VL intubation. Several methods have been described to overcome this problem, including the placement of a bougie into the trachea using VL, and then railroading the ETT over the bougie into the trachea. A bougie is a thin cylinder of rubber or plastic, metal or other material that is inserted into or through a body passageway, such as the esophagus, to diagnose or treat a condition, and can be used to widen a passageway, guide another instrument into a passageway, or dislodge an object. One method used to overcome failed advancement of the ETT into the trachea is to leave the ETT engaged in the glottis, remove the stylet, and advance a plastic bougie down the ETT and into the trachea, then railroad the ETT over the bougie. However, these methods can be complex and difficult. The difficulties can lead to multiple intubation attempts which can result in laryngeal injury and increased complications. A number of studies have correlated the increased risk of adverse events associated with multiple intubation attempts (Mort, *Anesthesia and Analgesia.* 2004; 99:607-13).

There remains a need for additional devices to assist proper insertion of ETT devices.

SUMMARY

Multiple intubation attempts leads to increased complications. These operators may particularly benefit from the stylet devices described herein. Further, the stylets described herein may provide a particular benefit to operators outside-of-the-operating room during emergency tracheal intubation, and in austere conditions encountered by EMS personnel, military medics, and critical care air transport teams.

Certain embodiments are directed to an intubation assist device or intubation stylet. Particular embodiments include an intubation stylet with an offset, ergonomic handle that provides for the operators wrist to remain more extended and elbow to remain more flexed which allows for a more comfortable and ergonomic positioning of the arm during intubation. The offset of the handle allows the operator to put their arm in a much more favorable position during intubation. Other aspects combine the offset handle design or a standard handle with various stylet designs described herein.

Stylets that can be used in conjunction with the offset handle or a standard handle can include hollow or solid stylets. In certain aspects the stylets can be rigid or semi rigid stylets. In still further aspects the distal region of the stylet can be modified. The distal region can be modified to include a variety of tips, lights, cameras, and or other functionalities. In certain aspects the handle can be modified to include a videoscreen or electronic monitoring components.

The offset handle can be associated with an ETT advancement component. The ETT advancement component being configured to moveably connect to and/or hold the ETT during insertion as well as being capable of applying force to advance the ETT along the long axis of the stylet and into the trachea. In certain aspect the offset handle and ETT advancement component are moveably connected by a track, groove, or the like. There may or may not be a ratcheting mechanism associated with the interaction between the handle and the ETT advancement component.

In certain aspects the offset handle can incorporate a bougie that can be advance to guide insertion of the ETT. The tip of the bougie can be soft ("safe-soft") and may or may not be malleable distally. The term "malleable" means that the section can be easily bent with the fingers and will retain its bent shape on its own without having to apply any external retaining force. Malleable is distinct from semi-rigid in that the amount of force needed to bend a malleable portion is less that than need to bend a semi-rigid portion.

In certain embodiments the offset handle is configured to be used with attachable/detachable stylets, with the stylets being disposable and the handle being reusable. In particular aspects the handle and the stylet are integrated and the whole device is disposable. In particular aspects the handle and the stylet are integrated and the whole device is reusable. In some instances, the device is configured to be used by one person during a laryngoscopy of a subject in that a bougie can be advanced and retracted and/or an ETT can be disengaged from the stylet by using the thumb of the hand holding the offset handle. In some instances, the device is configured to be used for laryngoscopy of a human. In some instances, the device is configured to be used for laryngoscopy of a non-human mammal subject.

The intubation stylets described herein can be configured to be used in conjunction with a video laryngoscopy (VL) device, a direct laryngoscopy (DL) device, or a dual purpose flexible laryngoscopy device. Each of these configuration can be used in conjunction with a standard straight tip, a malleable tip, or an offset tip. In certain aspects the tip is flexible and bends when encountering tissue in the larynx and trachea. In other aspects the tip maintains a memory or shape in that once positioned the tip can maintain the position of shape, e.g., an offset position. In still other aspects the tip can be permanently formed in an offset position.

The stylet can be a curved, hollow stylet incorporating an extendable bougie positioned in the lumen of the stylet. This device will allow the operator to place the ETT, utilizing the stiffness of the stylet component, at or near the glottic aperture and advance the integrated bougie from the stylet through the vocal cords. Once the bougie is in place the ETT is advanced over the bougie into the trachea. In some instances, the hollow stylet provides the appropriate curvature in order to engage the glottic aperture during VL, and the bougie provides proper (tracheal) directionality for the ETT while force is applied to the ETT by the operator, e.g., via an ETT advancement component. The bougie also directs the ETT downward and away from the anterior larynx or anterior trachea where it can hang up or stall.

The term "hollow stylet" as used herein includes rigid or semi-rigid hollow stylet configured to have a bougie passed through the lumen of the stylet. In certain aspects a stylet has a thin tube configuration. The hollow stylet can have an external diameter of from 2.0, 2.5, 3.0, 3.5, 4.0, 4.5, 5.0, 5.5, 6.0, 6.5, 7.0, 7.5, 8.0, 8.5, 9.0, 9.5 to 10.0 mm, including all values and ranges there between, and an internal diameter of 1.0, 1.5, 2.0, 2.5, 3.0, 3.5, 4.0, 4.5, 5.0, 5.5, 6.0, 6.5, 7.0, 7.5, 8.0, 8.5, 9.0, to 9.5 mm, including all values and ranges there between.

A "bougie" is a device used as a guide to aid insertion of other medical appliances (e.g., ETT) via the oral cavity or other potential anatomical space or opening. Typically the bougie is removed once the medical appliance is in place. The length of a bougie can vary from 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0 21.5, 22.0, 22.5, 23.0, 23.5, 24.0, 24.5, 25.0, 25.5, 26.0, 26.5, 27.0, 27.5, 28.0, 28.5, 29.0, 29.5, 30, 35, 40, 45, 50, 55, 60, 65, to 70 cm, including all values and ranges there between. Bougie outer diameters can vary from 1.0, 1.5, 2.0, 2.5, 3.0, 3.5, 4.0, 4.5, 5.0, 5.5, 6.0, 6.5, 7.0, 7.5, 8.0, 8.5, 9.0, to 10 mm, including all values and ranges there between The bougie may have a circular or elliptical cross section and can be made of a polymer such as aliphatic polyurethane, polytetrafluoroethylene, or other appropriate material. In certain aspects a bougie's flexibility or flexural modulus can changed along its length. For example the bougie can become more flexible as you move proximal to distal along its length. Each section having a specific flexural modulus, length and location along the bougie. For example the proximal end of the bougie can be more rigid than the distal end. A bougie can have a durometer in a range of about 20 Shore A to about 90 Shore A, as measured according to ASTM D2240. In certain aspects the flexible tip of a bougie can have a durometer from 20 shore A to 40 shore A. Other materials that can be used for the bougie include, but are not limited to, latex, silicon, polyester, nylon, rubber, and silk. In certain aspects the bougie material can comprise radiopaque or tracer material(s), such as barium sulphate. Specific examples of radiopaque materials include barioum diatrizoate, ethiodized oil, gallium citrate, iocarmic acid, iocetamic acid, iodamide, iodipamide, iodoxamic acid, iogulamide, iohexol, iopamidol, iopanoic acid, iprocemic acid, iosefamic acid, ioseric acid, iosulamide meglumine, iosumetic acid, iotasul, iotetric acid, iothalamic acid, iotroxic acid, ioxaglic acid, ioxotrizoic acid, ipodate, meglumine, metrizamide, metrizoate, propyliodone and thallous chloride. The material may be a shape memory material and may be self-lubricating.

In some instances, the intubation stylet contains a rigid or semi-rigid curved, hollow stylet with a proximal end and distal end; a flexible bougie with a handle, the bougie contained at least partially within the lumen of the hollow stylet and configured to be extended from and retracted into the distal end of the hollow stylet. The bougie handle can be configured to extend outside of the proximal end of the hollow stylet or be inserted into the hollow stylet up to a predetermined stop. In other aspects a stylet handle is attached to the proximal end of the hollow stylet. In other instances, the intubation stylet is coupled to a hollow endotracheal tube (ETT), wherein at least a portion of the hollow stylet is capable of being contained within or inserted into the lumen of the ETT, and wherein the ETT is capable of being extended past the distal end of the hollow stylet. The length and dimensions of the stylet can vary in relation to the length and dimension of the ETT. ETT internal diameters can vary from 2.0, 2.5, 3.0, 3.5, 4.0, 4.5, 5.0, 5.5, 6.0, 6.5, 7.0, 7.5, 8.0, 8.5, 9.0, 9.5 to 10 mm, including all values and ranges there between, to accommodate patients from premature infants to adult males. The length of an ETT can vary from 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0 21.5, 22.0, 22.5, 23.0, 23.5, 24.0, 24.5, 25, 26, 27, 28, 29, 30, 31, 32, 33, 34 to 35 cm, including all values and ranges there between. The internal diameter of a hollow stylet can vary from 1.0, 1.5, 2.0, 2.5, 3.0, 3.5, 4.0, 4.5, 5.0, 5.5, 6.0, 6.5, 7.0, 7.5, 8.0, 8.5, 9.0, to 9.5 mm, including all values and ranges there between, and an external diameter of a hollow stylet can vary from 2.0, 2.5, 3.0, 3.5, 4.0, 4.5, 5.0, 5.5, 6.0, 6.5, 7.0, 7.5, 8.0, 8.5, 9.0, 9.5 to 10.0 mm, including all values and ranges there between. The length of a stylet from handle to distal end can vary form 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0 21.5, 22.0, 22.5, 23.0, 23.5, 24.0, 24.5, 25.0, 25.5, 26, 27, 28, 29, 30, 31, 32, 33, 34, 35, 36, 37, 38, 39, 40, 41, to 42 cm, including all values and ranges there between. In some instances, the hollow stylet curve is a distal curve with an angle of between about 10, 20, 30, 40, 50 and 60, 70, 80, 90, 100, 110, 120 degrees over the distal 5, 6, 7, 8, 9, 10, 11, 12, 13, 14, 15, 16, 17, 18, 19, or 20 cm, including all values and ranges there between, of the stylet. In some instances, the hollow stylet curve is a distal curve with an angle of about 80 degrees over the distal 5, 10, 15, or 20 cm of the stylet. In some instances, the hollow stylet curve is a distal curve with an angle of between about 30 and 55 degrees over the distal 5, 10, 15, or 20 cm of the stylet. In some instances, the hollow stylet curve is a distal curve with an angle of 45 degrees over the distal 5, 10, 15, or 20 cm of the stylet. In other instances, the hollow stylet is semi-rigid in that it is capable of being bent by a user using his/her hands without kinking the stylet prior to insertion, yet retain its shape during use of the device during a laryngoscopy procedure (i.e., the stylet is semi-rigid). In certain aspects the degree of curvature is determined by the angle of elevation between the long axis and a second axis formed after the curve.

In another aspect, a method is disclosed for laryngoscopy of a subject using any of the devices described herein. In some instances, the method includes one or more steps, such as obtaining or using any one of the laryngoscopy stylet devices as described herein, in certain aspects an ETT can be pre-loaded thereon; placing the distal end of the stylet device into and/or directly in front of the glottis aperture of the subject; extending a flexible bougie past the distal end of the hollow stylet or placing the distal end of a solid stylet, through the vocal cords of the subject, and into the trachea; extending the ETT past the distal end of the stylet, through the vocal cords of the subject, and into the trachea; and removing the intubation stylet from the ETT. In some instances, the steps of the method are performed by one user. In some instances, the subject is a human. In some instances, the subject is a non-human mammal. One advantage to some of the intubation stylet designs described herein is that the advancement mechanism does not require the ETT to be inserted fully in the vocal chords because the advance of the ETT by the mechanism thrust or launch the ETT into the trachea.

Certain embodiments can include a tip of contrasting color and a soft consistency (Safe-Soft) that prevents the ETT cuff from obscuring the operators view during VL, provides excellent visual acquisition of the tip, and prevents trauma to anatomic structures; or a tip that prevents ETT hang-up on the anterior, subglottic portion of the larynx/trachea during advancement of the complex into the proximal trachea.

In some instances the device includes a curved stylet comprising a proximal end and distal end, and a soft and flexible tip connected to the stylet, the tip extending past the distal end of the stylet and configured to extend past a distal end of a endotracheal tube (ETT) loaded on the device. In certain aspects the stylet is solid. In other aspect the stylet is rigid, In further aspects the stylet has a covering over the core of the solid and/or rigid stylet that extends beyond the distal end of the core forming a soft or pliable distal region. The distal region can be 1, 2, 3, 4, 5, to 5, 6, 7, 8, 9, 10 cm in length and taper into a rounded tip. In some instances, the distal region is configured to extend 1 to 5 centimeters past a distal end of an ETT loaded on the device. In some instances, the tapered tip is configured to extend 3.5 centimeters past the distal end of an ETT loaded on the device.

In some instances, the stylet is coupled to a hollow endotracheal tube (ETT), wherein at least a portion of the stylet is capable of being contained within the ETT, and wherein the ETT can be moved along the long axis of the stylet and extended past the distal end of the stylet during an intubation procedure. In certain aspects the ETT is a double lumen ETT. In other instances, the intubation stylet is coupled to a hollow endotracheal tube (ETT), wherein at least a portion of the hollow stylet is capable of being contained within or inserted into the lumen of the ETT, and wherein the ETT is capable of being extended past the distal end of the hollow stylet. The length and dimensions of the stylet can vary in relation to the length and dimension of the ETT. ETT internal diameters can vary from 2.0, 2.5, 3.0, 3.5, 4.0, 4.5, 5.0, 5.5, 6.0, 6.5, 7.0, 7.5, 8.0, 8.5, 9.0, 9.5 to 10 mm, including all values and ranges there between, to accommodate patients from pre-mature infants to adult males. The length of an ETT can vary form 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0 21.5, 22.0, 22.5, 23.0, 23.5, 24, 25, 26, 27, 28, 29, 30, 31, 32, 32, 33, 34, 35, 36, 37, 38, 39, 40, 41, or 42 cm, including all values and ranges there between. The diameter of a solid stylet can vary from 1.0, 1.5, 2.0, 2.5, 3.0, 3.5, 4.0, 4.5, 5.0, 5.5, 6.0, 6.5, 7.0, 7.5, 8.0, 8.5, 9.0, to 9.5 mm, including all values and ranges there between. The length of a stylet from handle to distal end can vary form 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0 21.5, 22.0, 22.5, 23.0, 23.5, 24.0, 24.5, 25.0, 25.5, 26, 27, 28, 29, 30, 31, 32, 32, 33, 34, 35, 36, 37, 38, 39, 40, 41, or 42 cm, including all values and ranges there between. In some instances, the stylet curve is a distal curve with an angle of between about 10, 20, 30, 40, 50 and 60, 70, 80, 90, 100, 110, 120 degrees over the distal 5, 6, 7, 8, 9, 10, 11, 12, 13, 14, 15, 16, 17, 18, 19, to 20 cm, including all values and ranges there between, of the stylet. In some instances, the stylet curve is a distal curve with an angle of about 80 degrees over the distal 5, 10, or 15 centimeters of the stylet. In some instances, the stylet curve is a distal curve with an angle of between about 30 and 55 degrees over the distal 5, 10, or 15 centimeters of the stylet. In some instances, the stylet curve is a distal curve with an angle of 45 degrees over the distal 5, 10, or 15 centimeters of the stylet. In certain instances, the stylet is rigid in that it is not capable of being bent by a user using his/her hands and retains its shape during use of the device during a laryngoscopy procedure. In certain aspects the degree of curvature is determined by the angle of elevation between the long axis and a second axis formed after the curve.

In some instances, the device is configured to be used by one person during a laryngoscopy of a subject. In some instances, the device is configured to be used for laryngoscopy of a human. In some instances, the device is configured to be used for laryngoscopy of a non-human subject.

Certain embodiments are directed to methods for laryngoscopy of a subject using a solid stylet. In some instances, the method includes: obtaining a stylet device disclosed herein with an ETT loaded thereon, the in certain aspects the stylet has a distal region that tapers to a rounded tip and placing the tapered tip through the vocal cords and into the trachea of the subject; advancing the distal end of the ETT through the vocal cords of the subject using the ETT advancer mechanism, and into the trachea. In some instances, the steps of the method are performed by one user. In some instances, the subject is a human. In some instances, the subject is a non-human.

In other embodiments the devices described herein can be incorporated into a sterile cover or kit.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 11. Illustrates a stylet with a light tip.

DESCRIPTION

Figure 1:
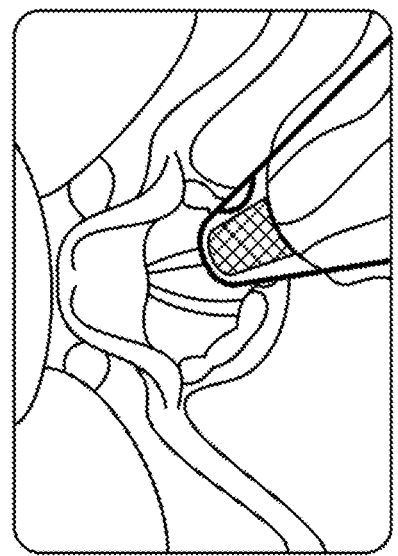
FIGS. 1A and 1B. (A) Illustrates a standard ETT-stylet configuration during video laryngoscopy. The ETT tip must be navigated into the glottic aperture (B) Illustrates the operator view of the ETT and larynx during video laryngoscopy.
Figure 1:
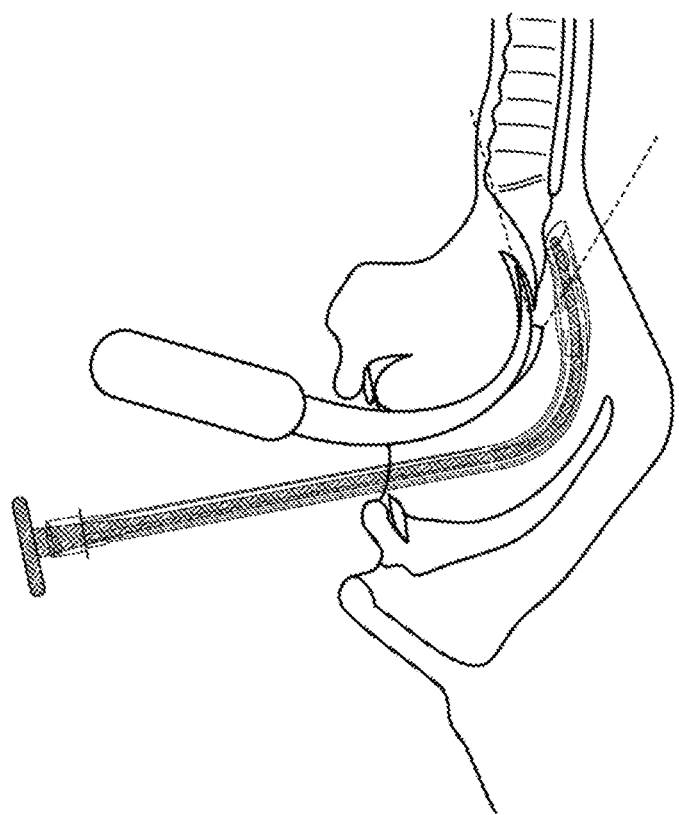
Figure 2:
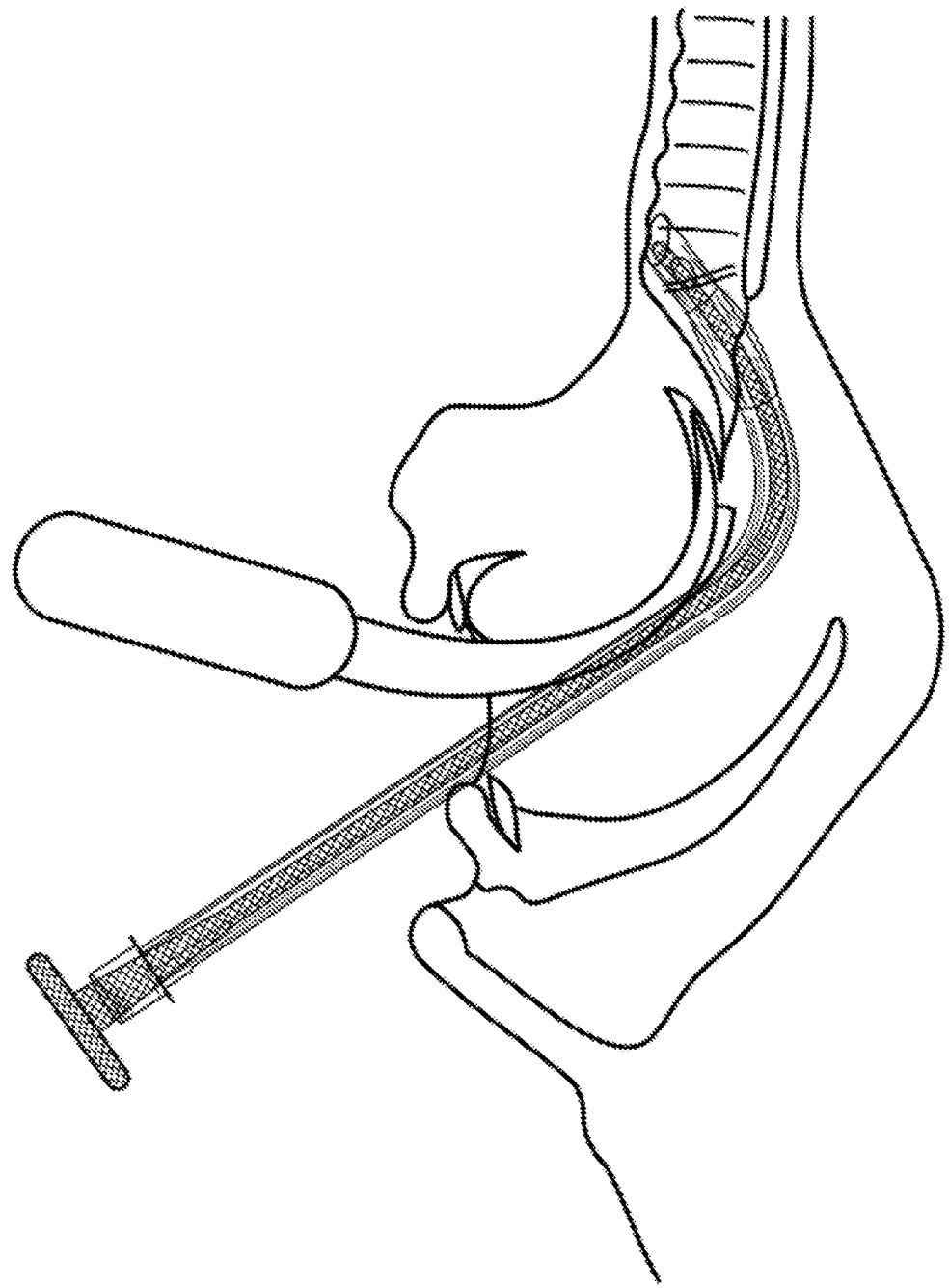
FIG. 2. Illustrates and ETT-stylet position after passing the ETT tip through the vocal cords. The ETT tip is colliding with the anterior subglottic trachea.

Millions of people every year undergo tracheal intubation. Most tracheal intubations are performed in operating rooms by anesthesiologists or nurse anesthetists, however tracheal intuabtion also occurs in the emergency department, intensive care units, hospital wards, and out-of-the-hospital. Within these later settings, the procedure is usually conducted under emergency circumstances. Direct laryngoscopy (DL) is likely the most prominent technique. However, the routine use of video laryngoscopy is increasing rapidly, as VL is present in nearly every operating room setting. The advent of VL has created new challenges that include occasional difficulty advancing the ETT into the trachea (tracheal cannulation) during the procedure. The ETT approach to the trachea during VL can be up to 90 degrees from axis of insertion at the mouth. This requires substantial curvature of the ETT and stylet. This limits the amount of axial force that the operator can apply to the ETT in order to advance it through the vocal cords. Also, the procedure is now performed via a video screen instead of direct vision. The cumulative effect confines the operator to a discontinuous, 2-dimensional space, a spatially off-axis target, and dampened haptic feedback. This necessitates more complex movements and skill in order to engage the glottic aperture. Furthermore, the resultant angle of the larynx and distal ETT can cause the ETT to collide with the anterior portion of the larynx impeding ETT advancement into the trachea. An unfavorable exposure of the glottic aperture with the video laryngoscope can exacerbate the problem. Solutions to these and other problems are presented by the intubation stylet designs presented herein.

I. Ergonomic Stylet Handle

Certain embodiments are directed to an offset handle. The offset handle can include a handle having a body, a front, a back, a top, and a bottom. The front of the handle is configured to accommodate one or more fingers of the user. The back of the handle is configured to accommodate or fit the palm of a user. The bottom is configured to contain or interact with a stylet. And the top can be configured to include a number of accessory members, e.g., a bougie advancement member, an ETT advance member, a visualization member, and the like. In certain aspects the handle can include an offset to improve the ergonomics of the handle. In some instances the offset handle includes an ETT advance member or mechanism. The ETT advancement member includes one or more thumb tabs configured to advance the ETT with respect to a stylet when force is applied to the thumb tab(s). The offset handle can be mechanically coupled to a tube (e.g., ETT) pusher device, which allows the operator to advance a tube being inserted by depressing the thumb tab(s) as they advance the ETT through the vocal cords. In some instances, a stylet is connected to or formed from the bottom of the stylet handle. In some instances, the offset handle can accommodate a bougie that can be easily advanced or retracted using a bougie handle at the proximal end of the bougie. In certain aspects a stop is provided on the far proximal end of the bougie. The stylet handle can be made of plastic, metal, plastic and metal, or other appropriate materials.

FIG. 3A-3D show various views of non-limiting embodiments of an offset or ergonomic handle 300. Handle 300 can have an integrated stylet 301 (i.e., permanently attached), or removeably attached or releasably connected stylet. The releasably connected stylet may include a bayonet coupling, threaded connection, latch, friction fit, tongue and groove arrangements, snap-fit, etc. that connects the handle 300 and the stylet 301. The handle can also be configured with an integrated bougie (see for example FIG. 4).

Figures 3A, 3B, 3C:
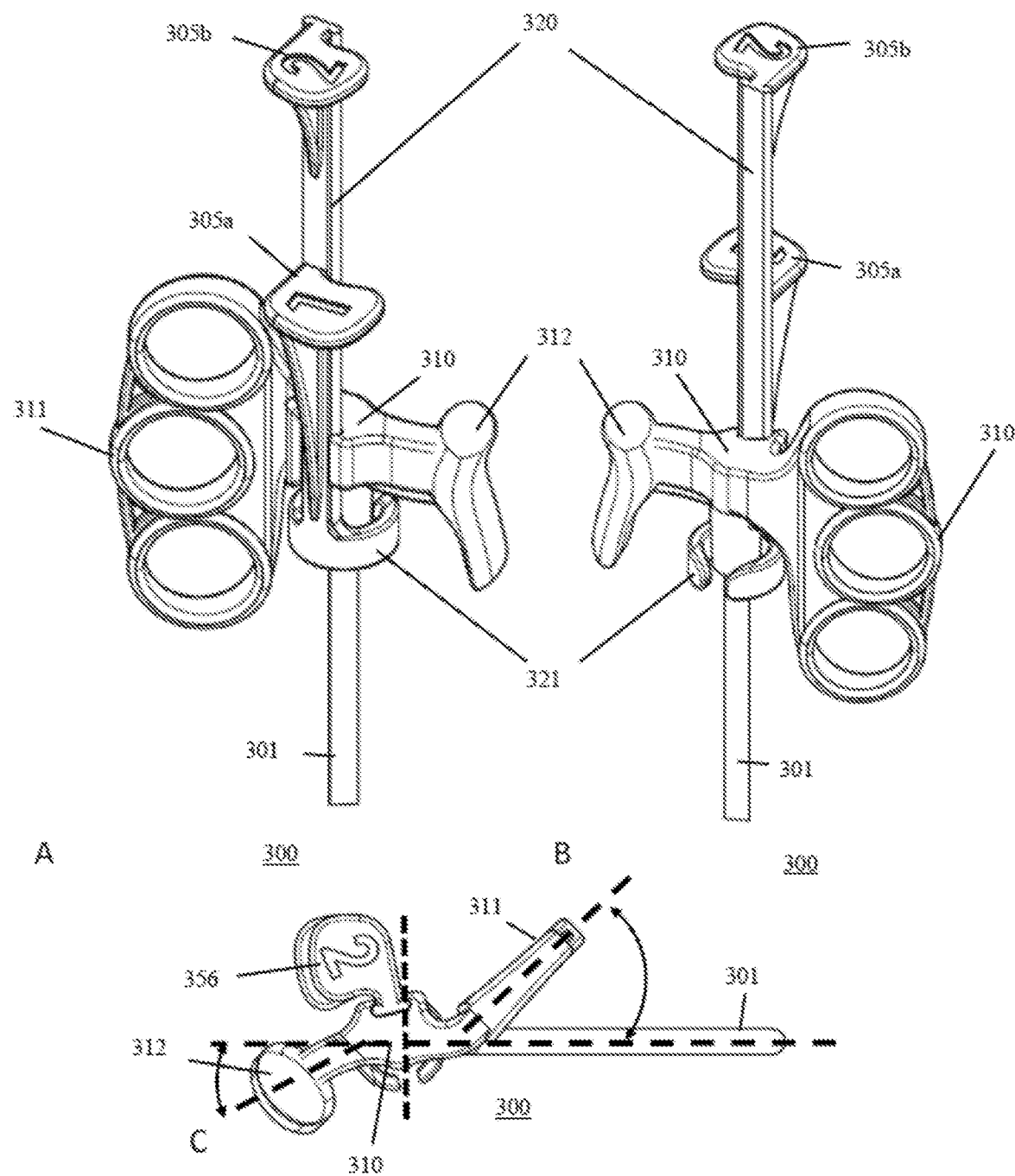
FIGS. 3A and 3B. Illustrates one embodiment of an offset handle configured as a intubation assist device. (A) is a first side view of an offset handle. (B) is a second side view of an offset handle. (C) is a top view of an offset handle. (D) is a side view of an offset handle and stylet portion forming a laryngoscopy assist device.
Figure 3D:
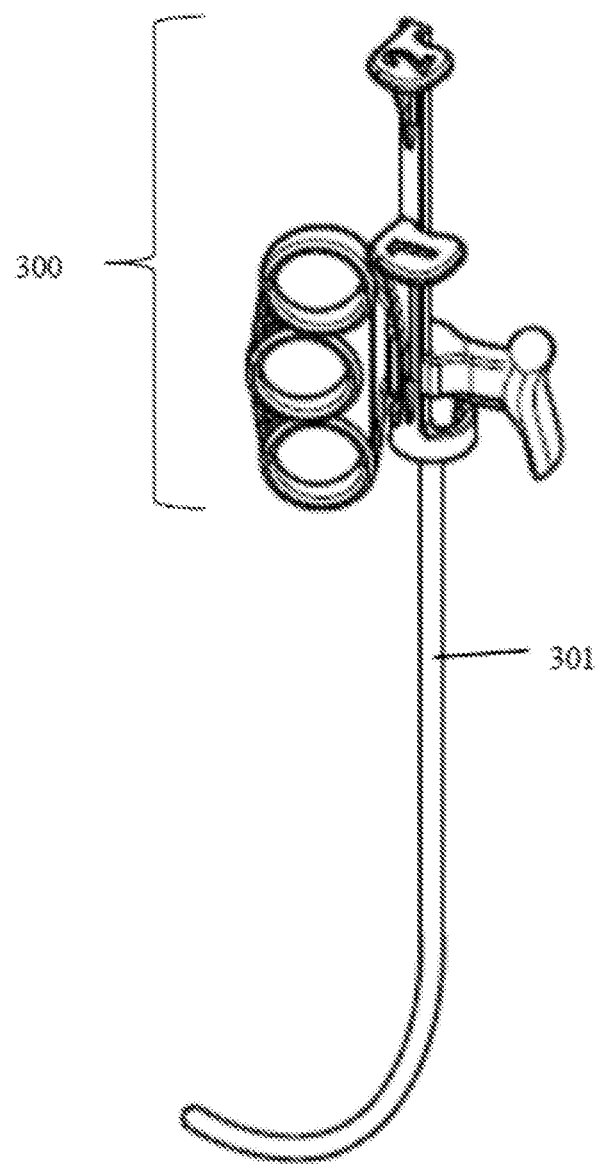
Figure 9:
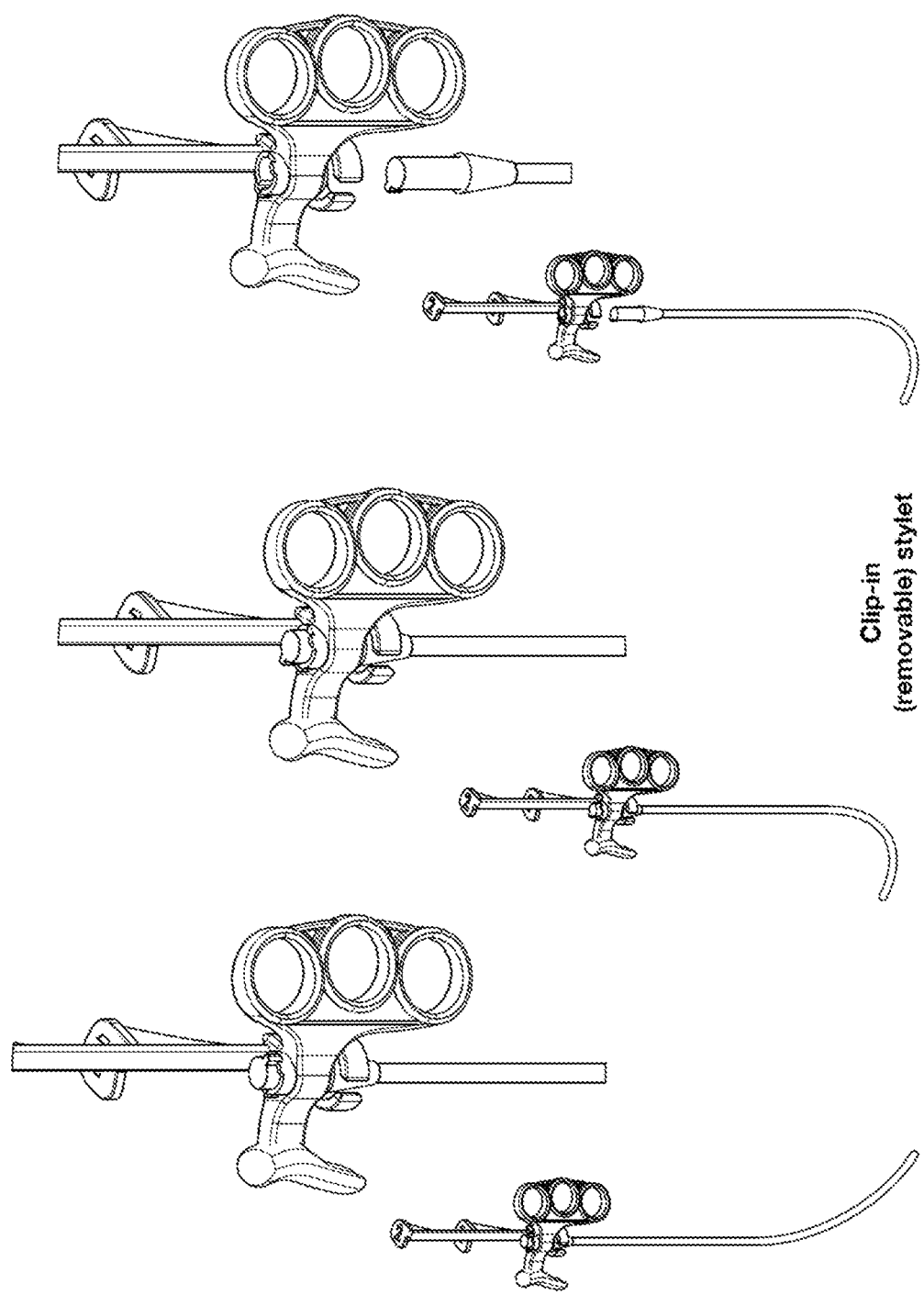
FIG. 9. Illustrates intubation stylet configured with an attachable/detachable stylet.
Figure 10:
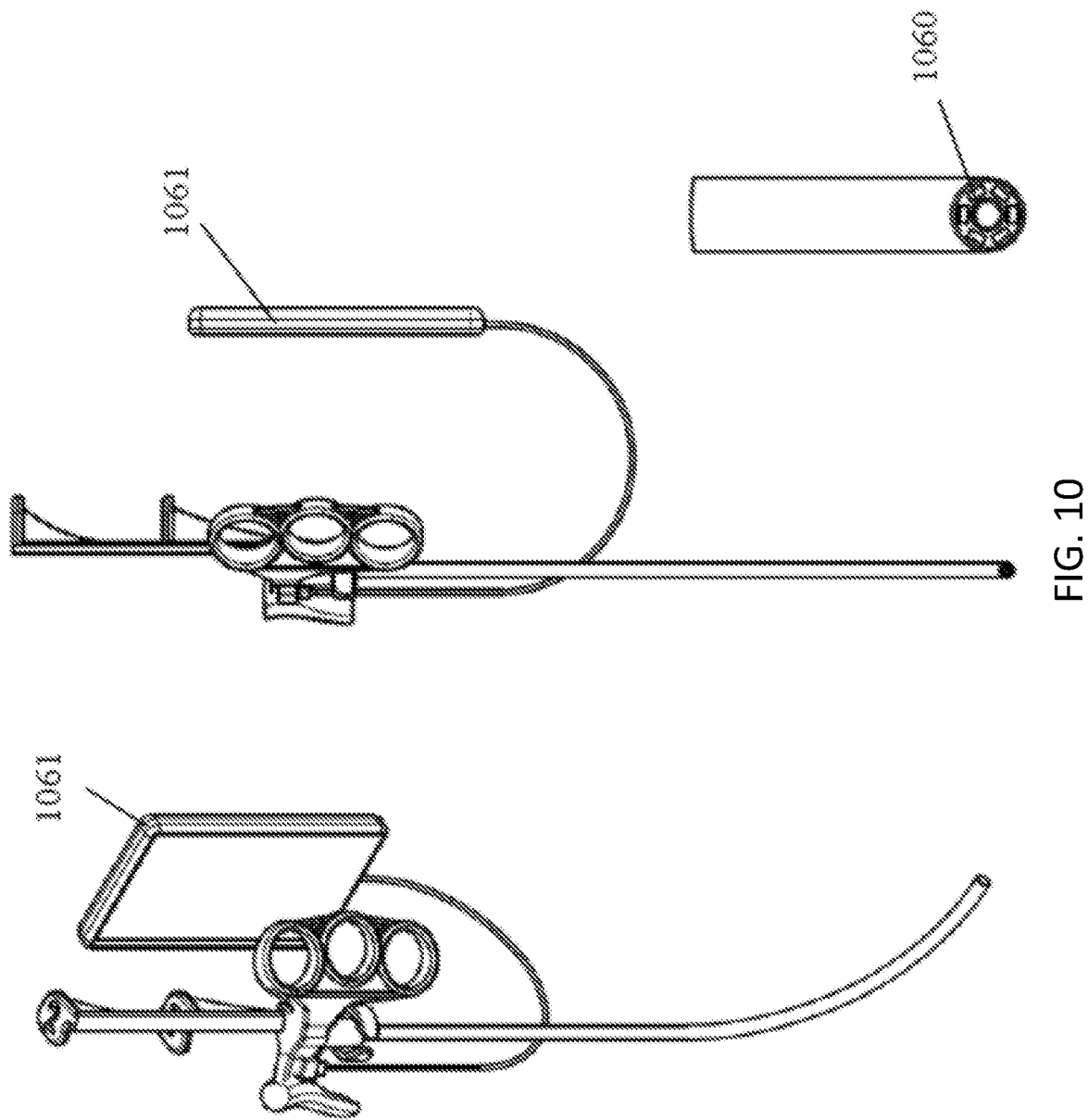
FIG. 10. Illustrates a stylet with a camera tip.

When viewed from the top (FIG. 3C) the ergonomic handle 300 has a long axis which is perpendicular to the long axis of a stylet 301. Offset handle 300 comprises a first end forming handle front 311 and a second end forming handle back 312 connected by handle body 310. Handle front 311 can be configured to have 1, 2, 3, or 4 finger loops or grooves. In particular instances the handle front has three finger loops or grooves. In particular aspects the finger loops or grooves are configured to receive the index finger, middle finger, and fourth finger, excluding the pinky and thumb. Handle back 312 can be configured to fit into the palm of the hand engaging the offset handle, providing support when the handle is gripped. In certain aspects the support from the finger loops or grooves can allow for release of the back of handle providing enough mobility to the hand and thumb so that the operator can reach and engage the thumb tabs of the ETT advancement device. The offset can be measured as an angle formed, as viewed from the top, through handle body 310 in line with stylet 301 and an axis formed along the length of the projection forming the front handle as viewed from the top (see FIG. 3C), the offset allows the operator to position their arm in a much more favorable position during the ETT insertion process. In certain aspects the front of the handle is offset by 10, 20, 30, 40, 50, or 60 degrees, including all values and ranges there between. In particular aspect the front of the handle is offset by about 45 degrees. In certain aspects the back of the handle is offset by 10, 20, 30, or 40 degrees, including all values and ranges there between. In particular aspect the back of the handle is offset by about 20 degrees. Variation of the offset handle can be used in combination with standard stylets and the novel stylets described below. In a further aspect stylet 301 is permanently attached or integrated with handle 300. In certain aspects handle body 310 can be configured to receive and releasably connect to stylet 301 (see FIG. 9 for an example). Ergonomic handle 300 and stylet 301 can be releasably connected by a bayonet coupling, a threaded connection, a latch, a friction fit, a tongue and groove arrangement, a snap-fit, etc. FIG. 3D illustrates such a handle 300 coupled with stylet 301.

Offset handle 300 can include an ETT advancement member 320. The ETT advancement member can be configured to engage an ETT that is to be insert into the trachea of a subject. The ETT advance member provides one or more thumb tabs for advancement of an ETT using pressure applied by the thumb. In certain aspects the handle and stylet are loaded with an ETT tube, the stylet being inserted in the lumen of the ETT tube and held in place by a ETT connector/holder (e.g., 321). ETT advancement member 320 is moveable in a direction that is parallel to the long axis of stylet 301. Thumb tab(s) (322a, 322b) on the proximal end of the member is/are configured to receive a force applied by the users thumb to move the ETT advancement member 320 along the long axis of stylet 301 towards the distal end of stylet 301. The distal end of the ETT advancement member 320 can include an ETT connector/holder 321. By advancing the ETT advancement member 320 the stylet 301 and handle 300 are separated from an ETT during ETT insertion. There can be one, two or more thumb tabs, preferably two. In certain aspects there will be at least one thumb tab on the end distal to a portion configured to connect to the ETT (ETT connector or holder portion) and at least a second thumb tab between the first thumb tab and the ETT connector portion/holder, this configuration provides for incremental advancement using a single hand holding the handle. In certain aspect the handle 300 and ETT advancement member 320 are connected by a track configured to guide or push the ETT along the stylet. There may or may not be a ratcheting mechanism associated with the interaction between the handle and the ETT advancement member 320. There may or may not be a mechanism that prevents the ETT advancement member 320 from detaching from the handle 300 after the operator has fully advanced member 320.

Figure 6:
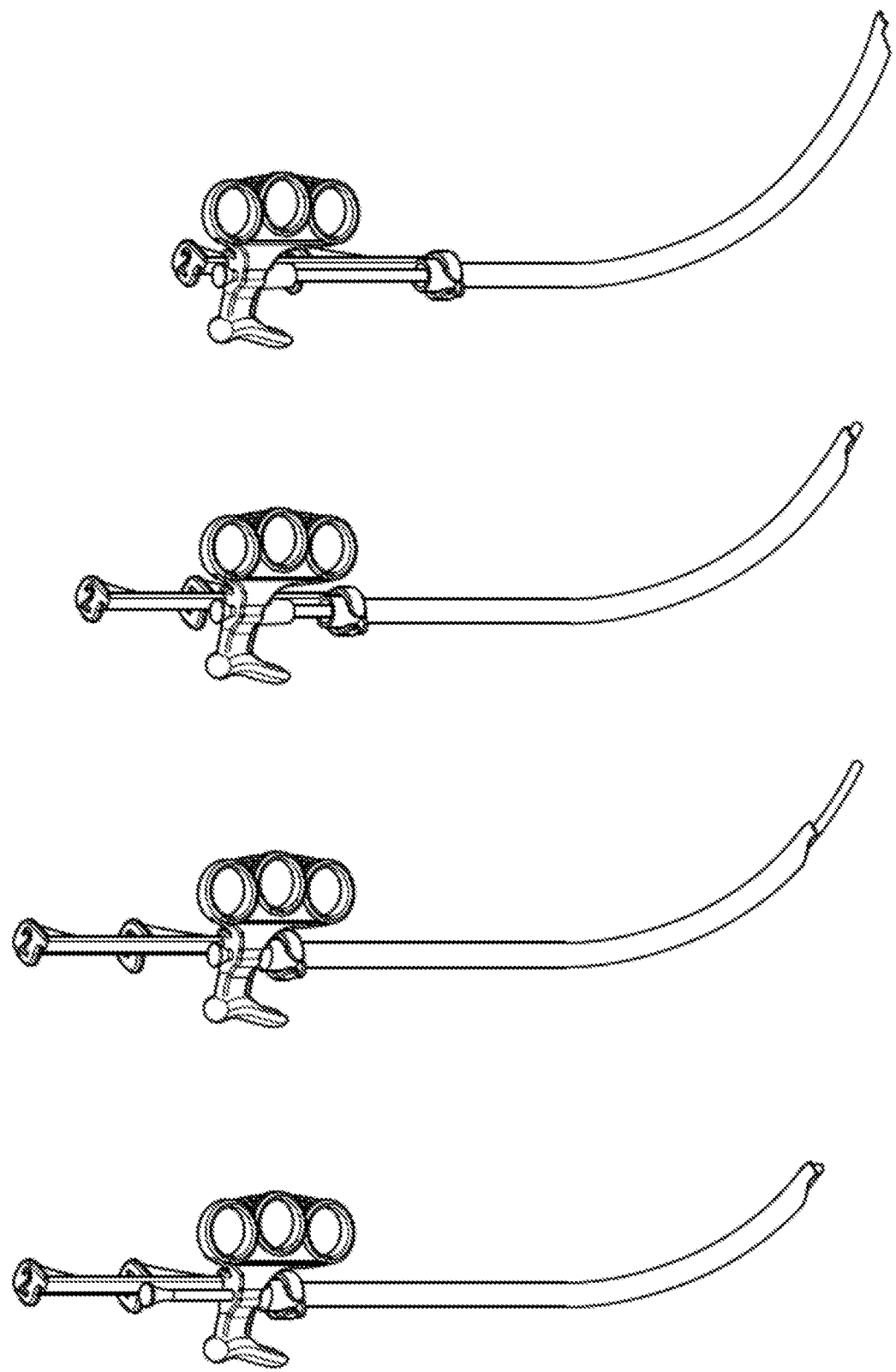
FIG. 6. Illustrates an intubation stylet engaged with an ETT and snapshots of the ETT being advanced along the stylet.

FIG. 6 shows the use of an ETT advancement member in the deployment of an ETT. FIG. 6A shows a fully loaded intubation stylet device (stylet device and an ETT). FIG. 6B shows the deployment of a bougie to guide insertion through the vocal chords. FIG. 6C shows a initial advancement of the ETT by depressing thumb tab 1. FIG. 6D shows fully advanced ETT after depressing thumb tab 2, after which the assist device is removed.

II. Intubation Stylet Devices

The intubation stylet devices include a handle portion and a stylet portion. Stylets can be classified generally as hollow stylets and solid stylets, each of which can be adapted to be used with an offset handle or a standard stylet handle. Stylets can be made of metal, plastic, or a combination thereof. In a further aspect the exterior surface of a stylet can be, but need not be, coated or otherwise treated. In various embodiments the stylet is coated with a plastic or nylon coating. In certain aspects stylets, either hollow or solid, can be an elongated tube or cylinder with a distal bend of approximately 10, 45, 50, 60, 70, 80, 90, 100, 110 or 120 degrees, including all values and ranges there between.

A. Hollow Stylets

Figure 5:
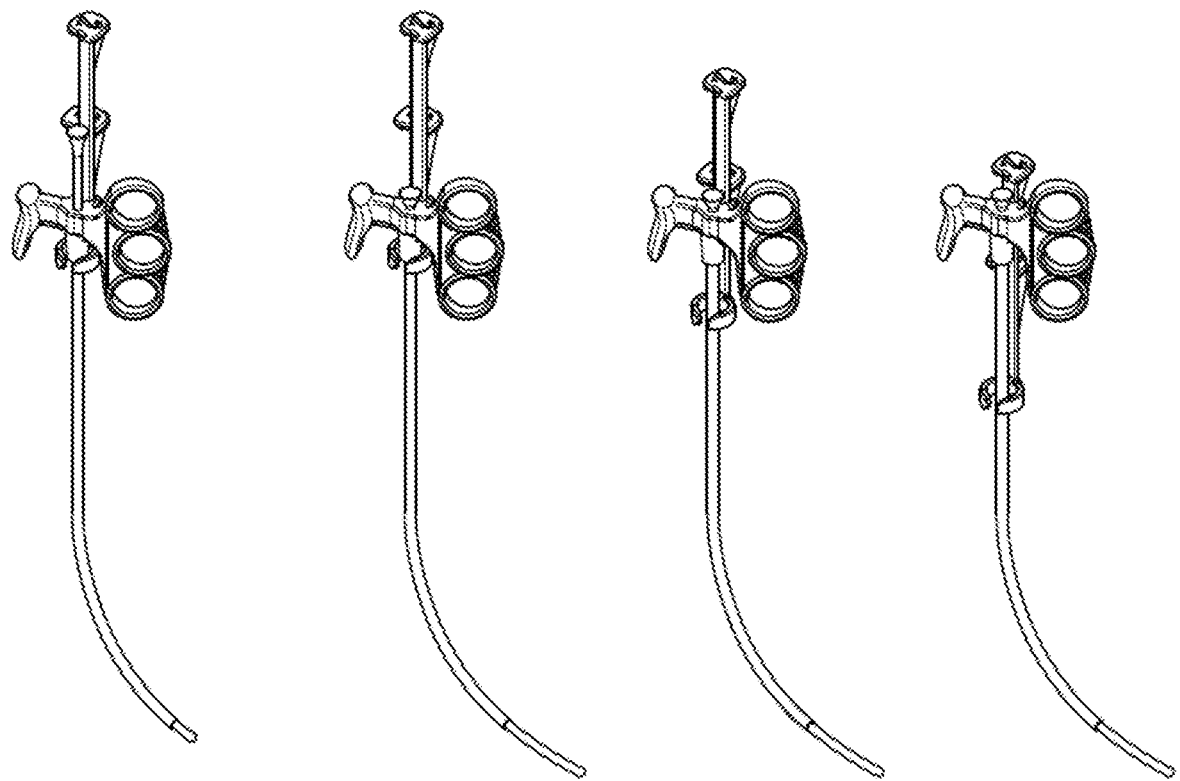
FIG. 5. Illustrates an intubation stylet with an integrated bougie and snapshots of the bougie being advanced along the stylet in conjunction with the ETT advancement mechanism being engaged.
Figure 7:
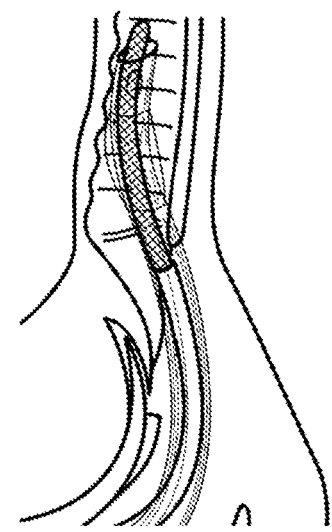
FIG. 7. Illustration of an BILS stylet intubation procedure.
Figure 7:
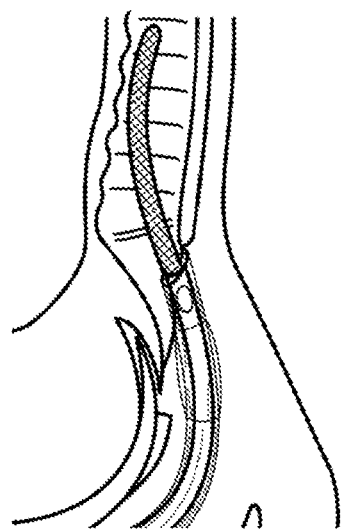
Figure 7:
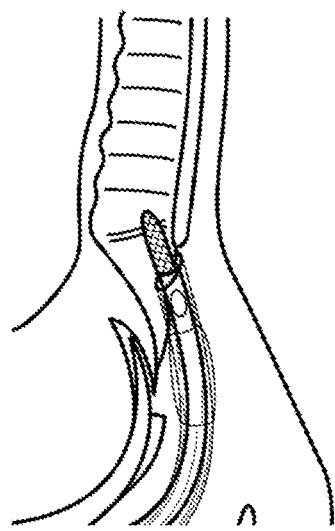

In some instances, the devices described herein have a curved, hollow stylet that can incorporate an extending or telescoping bougie in the lumen of the stylet (Bougie Integrated Laryngoscopy Style, BILS). In some instances, this will allow the operator to place the ETT and stylet at or near the glottic aperture, advance the narrow, integrated bougie through vocal cords, then advance the ETT over the bougie into the trachea (see FIG. 5, FIG. 6, and FIG. 7). In some instances, the hollow stylet provides the appropriate curvature in order to engage the glottic aperture during VL, and the bougie provides proper (tracheal) directionality for the ETT while axial force is applied to the ETT by the operator (FIG. 7). The bougie also directs the ETT downward and away from the anterior larynx where it can sometimes hang up. These hollow stylets can be used in conjunction with the offset handle described above and one or more of the additional features described herein.

Figure 4:
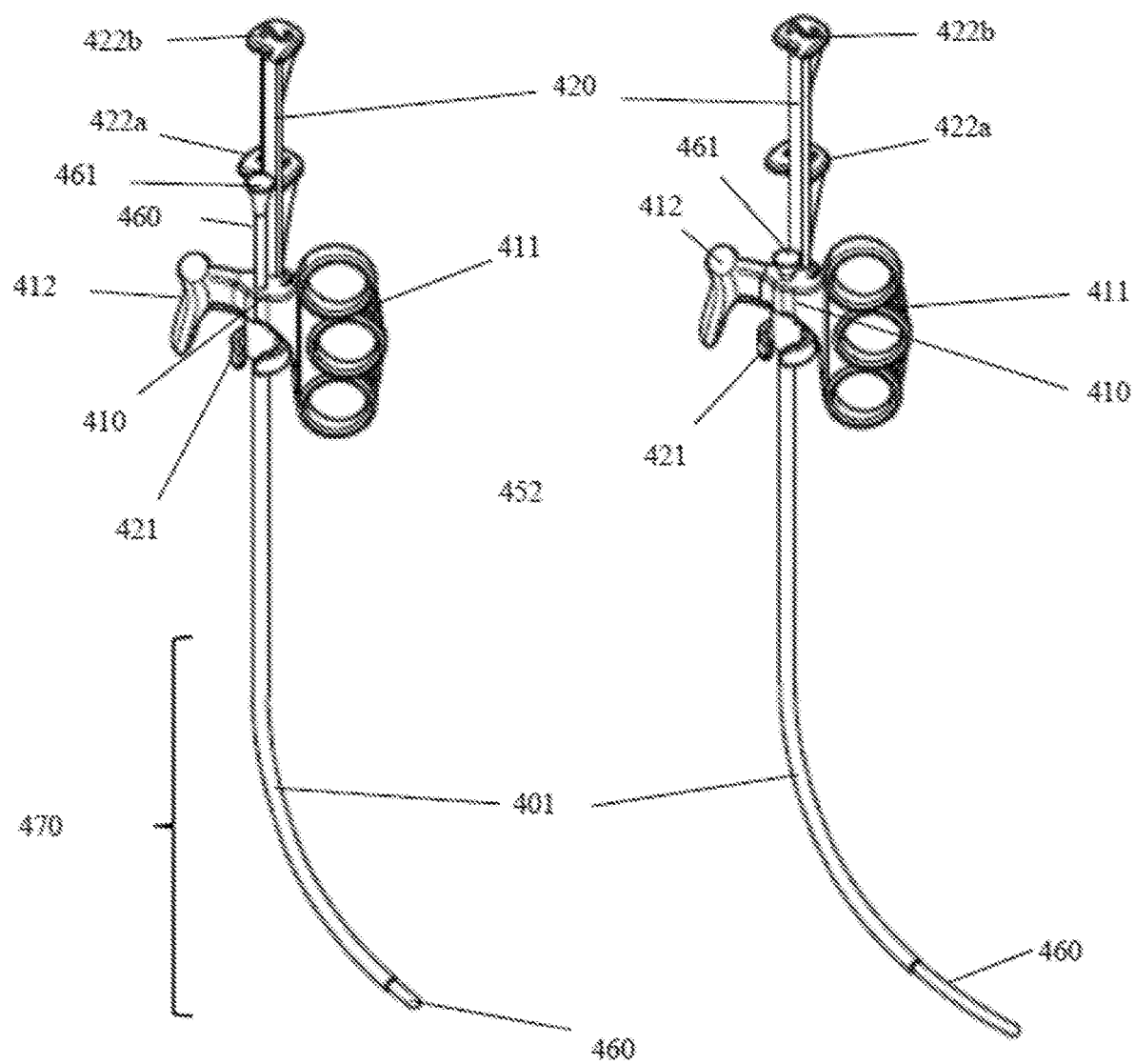
FIGS. 4A and 4B. (A) Illustrates one embodiment of an intubation assist device incorporating an integrated bougie.

FIG. 4 shows a non-limiting embodiment of a bougie integrated handle. The device illustrated in FIG. 4 comprises hollow stylet 401 coupled to stylet handle 400 and bougie 460 moveably positioned in the lumen of the stylet. Offset stylet handle having a member perpendicular to the long axis of stylet 401 and a thumb tabs (422a, 422b) that are configured to receive a force applied by the users thumb to separate stylet 401 from an ETT during ETT insertion. In one embodiment configured for video laryngoscopy, the device has a slow, elongated distal bend 470 of approximately 10 to 120 degrees. In certain aspects the intubation stylet can be configured for direct laryngoscopy in that the device that can have a shorter curved portion having a curve of approximately 45 degrees. The hollow stylet portion can be semi-rigid in that the stylet can be adjusted by bending the distal portion of the stylet to facilitate intubation during VL or DL. Region 470 can be made from a semi-rigid material that can be bent to a desired curvature and maintain that curvature once bent.

In some instances, a hollow stylet can be connected to a stylet handle described above. The stylet can be removeably connected to or integrated into the handle. One or more thumb tabs can allow the operator to advance the ETT with the thumb of the hand holding the handle (typically the right hand) as they advance the ETT through the vocal cords. In some instances, the stylet is a metallic and/or plastic hollow stylet. In some instances, within the hollow stylet is a malleable bougie that can be easily advanced or retracted using a small bougie handle at the proximal end of the bougie. In certain aspects a stop is provided on the far proximal end of the bougie. In certain aspects the bougie is designed to have different flexibility at different points or regions along its length. In certain aspects the bougie can have a durometer of 20 Shore A to 80 Shore A. In other aspects the bougie can have a graded durometer that terminates in a distal portion having a durometer of 20 Shore A to 40 Shore A. in certain aspects the proximal segment of the bougie is semi-rigid or rigid and the distal 1, 2, 3, 4, 5, 6, 7, 8, 9, 10 cm is flexible having a durometer of less than 40 Shore A, and more preferably 20 Shore A or values there between.

Figure 8:
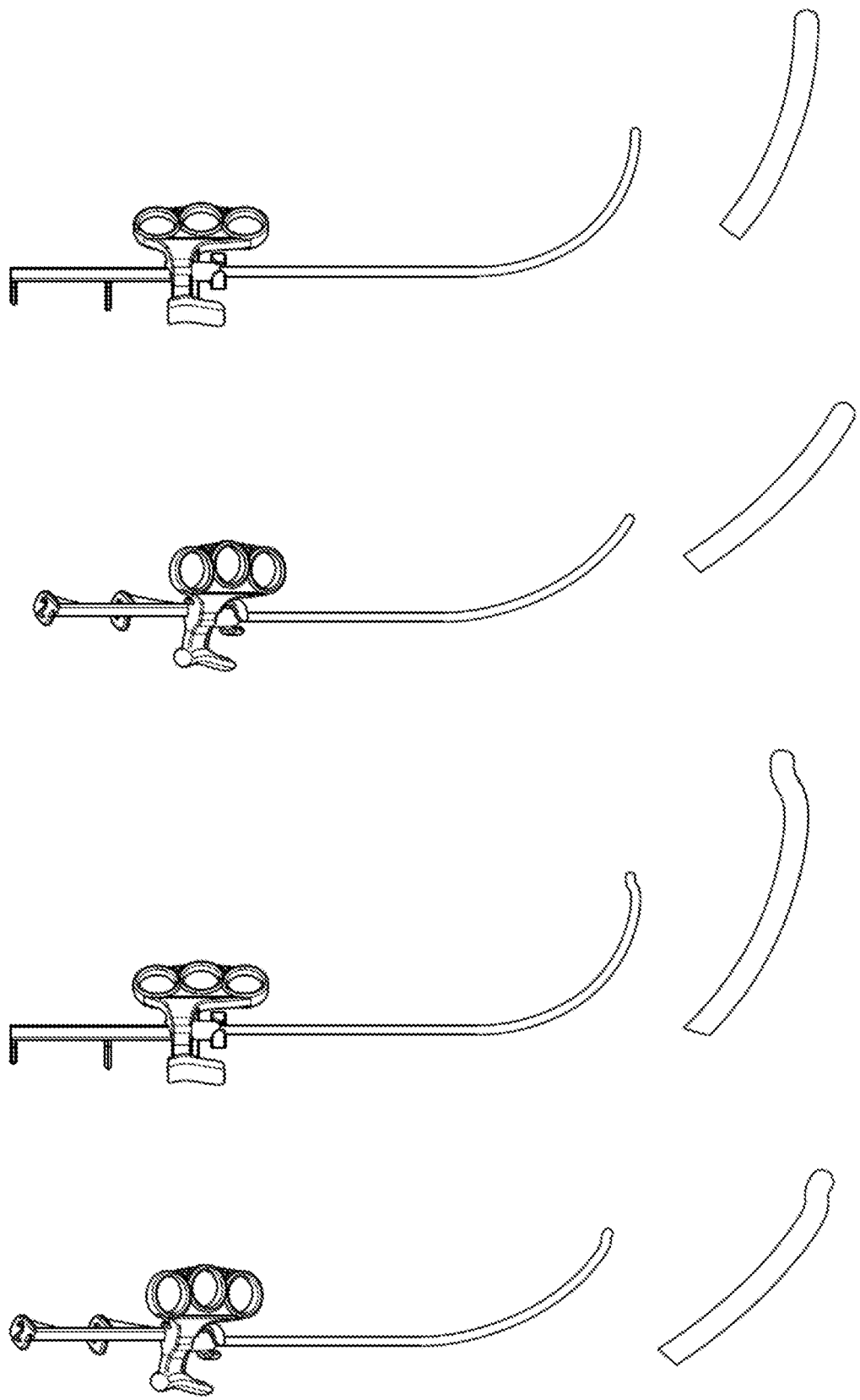
FIG. 8. Illustration of embodiments of various tips that can used in conjunction with the intubation stylets described herein.

A bougie may or may not comprise a rod of a elastomeric material which combines stiffness with flexibility at body temperatures. In some instances, the bougie is very soft at its most distal end, i.e., the bougie has a "Safe-Soft" tip (e.g., the distal 2, 3, 4, 5, or 6 cm of the bougie). Certain embodiments of the "Safe-Soft" tip are illustrated in FIG. 8. FIG. 8 shows a standard tip that is essentially straight and an offset Soft-Safe tip that has the terminal portion in an offset configuration. The soft end can minimize the possibility of airway injury during advancement of the bougie. In some instances, the distal end of the bougie is slightly bulbous having an external diameter larger than the internal diameter of the hollow stylet so it cannot be retracted fully into the stylet by the operator, nor can it be pushed back into the stylet during the intubation procedure. In some instances, the bougie (460) has a small handle or stop or button (461) at the proximal end that the user or an assistant can push to advance the bougie. Stop 461 can also serve to prevent excessive advancement of the bougie into the patient or loss of the bougie into the ETT or the patient.

FIG. 6 illustrates an intubation procedure using devices described herein. In some instances, the laryngoscopy device can be used by obtaining a glottic view using VL in the standard manner. The device, with a loaded ETT, can then be carefully placed into the airway according to standard VL practice. The operator then places the tip of the hollow stylet/ETT into or directly in front of the glottic aperture. The operator then advances the inner bougie into the trachea with their thumb on the widened portion (or button) of (on) the proximal end of the bougie. The operator then presses the lower thumb tab on the advancement member to begin advancing the ETT in to the trachea. The operator then presses the upper thumb tab to further advance the ETT into the trachea. The operator then grasps the ETT and backs out and outwardly rotates the stylet device in order to remove it from the ETT. Grasping of the ETT and/or the rotation and removal of the stylet device can be accomplished by the operator or an assistant in a maneuver similar to that used by assistants during current VL and DL procedures. Once the ETT is within the trachea and is properly positioned, a cuff on the ETT can be inflated in the usual manner.

In some instances and as illustrated in FIG. 7, embodiments of the device disclosed herein can be used during video laryngoscopy. FIG. 7 illustrates the insertion of ETT using a stylet as described herein that is position in the lumen of ETT being inserted into a patient with the assistance of a laryngoscope. FIG. 7 shows that an operator can steer ETT towards the glottic aperture, direct soft-tipped bougie through the vocal cords, and glide ETT into the trachea with unparalleled ease. The devices described herein can help overcome the challenge encountered in advancing ETT into the trachea during VL despite an adequate view of the vocal cords. The devices can also facilitate VL intubation during less than optimal VL views. Likewise, some embodiments of the device disclosed herein can be used to facilitate tracheal intubation during direct laryngoscopy (DL) under less than ideal intubating conditions. The devices decried herein can be of particular benefit to operators outside-of-the-operating room during emergency tracheal intubation, and in austere conditions encountered by EMS personnel, military medics, and critical care air transport teams.

In some instances, the device can be used on a human subject, a non-human mammal subject, or a non-mammal animal subject.

B. Solid Stylets

Other embodiments are directed solid stylets without an inner bougie. Solid stylets can include one or more of (a) a pre-curved rigid stylet (metal or hard plastic); (b) a pre-curved metal stylet with a slick plastic or nylon coating; and (c) a malleable semi-rigid, user configurable stylet, with a metallic core, and a slick plastic or nylon coating. The solid stylet can include a modified distal portion or tip, including one or more modification described below. Solid stylets can be integrated into the handle or may be releasably connected to the handle. In particular embodiments a device comprising a solid stylet can be sterilizes and reused.

III. Stylet or Bougie Modifications

Stylets or bougies of the invention can include modifications to the body and/or modification to distal end or tip.

A. Stylet Flexibility/Malleability

Rigid stylet. The hollow or solid stylet can be manufactured to be rigid. In particular aspects the solid stylet comprises is rigid or includes a rigid portion. The term "rigid" means incapable of or resistant to bending. In certain aspects a rigid material can have a durometer above 80 shore A.

Semi-rigid stylet. The hollow or solid stylet can be manufactured to be semi-rigid. In particular aspects the hollow stylet is semi-rigid or includes a semi-rigid portion. The term "semi-rigid" as used herein means sufficient rigidity to maintain a given position when flexed into that particular position or shape by application of force to the stylet. In certain aspects semi-rigid material can have a durometer of 40 to 80 shore A.

B. Tips

The distal end of the stylet can terminate in a tip, which is a region design to minimize damage to the tissues of the glottis and/or the trachea during insertion. Each of these configuration can be used in conjunction with a standard tip that is a straight or offset or capable or malleable. The distal region or tip can be 1, 2, 3, 4, 5, to 5, 6, 7, 8, 9, 10 cm in length and taper into a rounded tip.

Soft tip. A soft and flexible tip allows operators to safely engage and enter narrow glottic apertures. A soft tip can prevent ETT hang up on the anterior sub-glottic larynx, which commonly occurs during VL. The distal end of a stylet or bougie that is soft, flexible, and/or tapered can extend past the distal end of an ETT loaded on the stylet, which is designed to minimize soft tissue and laryngeal injury. In certain aspects the soft tip has a durometer from 20 shore A to 40 shore A.

Malleable tip. In certain aspects a soft tip can have a malleable core that allows an operator to position and change the shape of the tip with the tip retaining the position or shape.

Offset tip. In other aspects the tip can be a preformed anatomic that has an offset, i.e., the distal portion is not in the same axis as the proximal portion of the tip.

C. Light Tip

In certain aspects a stylet can include a light or laser at the distal end of the stylet in order to illuminate/target the glottis.

D. Camera Tip

In other aspects a stylet can include a camera at the distal end of the stylet to visualize the glottis during the insertion procedure.

IV. Stylet Kits

In certain embodiment the stylet device described herein can be included in a pre-sterilized medical procedure kit and used for various medical procedures. In certain aspects sterilized procedure kits are provided with a plurality of components used in connection with a particular medical procedure. Certain embodiments are directed to sterilized kits to maintain a sterial environment or reduce the risk for infection during a procedure. Any materials that will be in contact with the patient can be provided in sterial compartments or packaging that can be opened just prior to use in order to maintain sterility or reduce contamination.

The stylet devices described herein can be used for VL and DL inside or outside the operating room setting. VL use has particularly expanded in the settings of out-of-the-operating room and out-of-hospital tracheal intubation. In these settings, non-anesthesiology personnel are usually the operators, and they have varying degrees of airway management skill and experience. These operators may particularly benefit from a device like those described herein. Therefore, the devices can be used in the operating room, emergency room, intensive care units, on location medial emergencies by EMS/Fire units, military field and air transport applications.

The invention claimed is:

1. An ergonomic stylet handle comprising:
   (a) a handle having a body between a front, a back, a top, and a bottom, wherein (i) the front of the handle is configured to accommodate one or more fingers of a user, (ii) the back of the handle is configured to accommodate or fit a palm of the user, (iii) the bottom of the handle is configured to contain or be coupled with a stylet, wherein the front, the back, or the front and the back of the handle are offset relative to a horizontal long axis of the handle body to improve the ergonomics of the handle; and
   (b) an endotracheal tube (ETT) advancement member having a proximal and distal end, wherein the proximal end is configured to provide for application of force along a length of the member and the distal end is configured to interact with an ETT, wherein the proximal portion of the ETT advancement member includes one or more thumb tabs.

2. The handle of claim 1, wherein the front of the handle is offset from the body of the handle by 10 to 60 degrees.

3. The handle of claim 1, wherein the front of the handle is offset from the body of the handle by 40 to 50 degrees.

4. The handle of claim 1, wherein the back of the handle is offset.

5. The handle of claim 1, wherein the front has 1, 2, 3, or 4 finger loops or grooves.

6. The handle of claim 1, wherein the top can be configured to include a number of accessory members.

7. The handle of claim 6, wherein the accessory member is a bougie advancement member, or a visualization member.

8. The handle of claim 1, further comprising a bougie that is configured to be advanced through the handle.

9. The handle of claim 1, further comprising a stylet.

10. The handle of claim 9, wherein the stylet is releasably connected to the handle.

11. The handle of claim 10, wherein the stylet is releasably connected by a bayonet coupling, a threaded connection, a latch, a friction fit coupling, a tongue and groove arrangement, or a snap-fit coupling.

12. An intubation device comprising:
    a curved, stylet comprising a proximal end and distal end;
    a flexible bougie, the bougie configured to be capable of being extended and retracted; and
    a stylet handle attached to the proximal end of the stylet, wherein the stylet handle is an ergonomic stylet handle comprising a handle having a body, a front, a back, a top, and a bottom, wherein (i) the front of the handle is configured to accommodate one or more fingers of a user, (ii) the back of the handle is configured to accommodate or fit a palm of the user, (iii) the bottom of the handle is configured to contain or be coupled with a stylet, wherein the front, the back, or the front and back of the handle are offset relative to a horizontal long axis of the handle body to improve the ergonomics of the handle.

13. The device of claim 12, further comprising a hollow endotracheal tube (ETT), wherein at least a portion of the stylet is capable of being contained within the ETT, and wherein the ETT is capable of being extended past the distal end of the stylet.

14. The device of claim 12, wherein the stylet curve is a distal curve with an angle of between 10 and 120 degrees.

15. The device of claim 12, wherein the stylet is capable of being bent by a user and retain its shape during use of the stylet during a laryngoscopy procedure.

16. A method for laryngoscopy of a subject having a glottic aperture, vocal cords, and a trachea, the method comprising:
    obtaining an intubation device of claim 12 with an endotracheal tube (ETT) loaded thereon;
    placing the distal end of the stylet into and/or directly in front of the glottic aperture of the subject;
    extending the flexible bougie past the distal end of the stylet, through the vocal cords of the subject, and into the trachea;
    extending the ETT past the distal end of the stylet, through the vocal cords of the subject, and into the trachea; and
    removing the intubation device from the ETT.

\* \* \* \* \*